United States Patent [19]

Reichler et al.

[11] 4,198,484
[45] Apr. 15, 1980

[54] CUVETTE AMPULE FOR USE WITH AUTOMATIC ANALYZER APPARATUS

[75] Inventors: Allen S. Reichler; Larry E. Swaton, both of Dallas, Tex.

[73] Assignee: Abbott Laboratories, North Chicago, Ill.

[21] Appl. No.: 928,114

[22] Filed: Jul. 26, 1978

[51] Int. Cl.² .................... C12M 1/24; G01N 21/24; C12Q 1/04
[52] U.S. Cl. .................................. 435/296; 435/299; 435/34; 356/246; 422/61; 422/102
[58] Field of Search ................ 195/139; 356/246, 244; 422/61, 102

[56] References Cited

U.S. PATENT DOCUMENTS

| | | | |
|---|---|---|---|
| 3,718,439 | 2/1973 | Rosse et al. | 422/102 X |
| 3,759,374 | 9/1973 | Helger | 356/246 X |
| 3,897,216 | 7/1975 | Jones | 356/246 X |
| 3,994,594 | 11/1976 | Sandrock et al. | 422/102 X |
| 3,998,594 | 12/1976 | Horne | 356/246 X |
| 4,013,368 | 3/1977 | Acker et al. | 356/246 |

Primary Examiner—R. B. Penland
Attorney, Agent, or Firm—Merriam, Marshall & Bicknell

[57] ABSTRACT

A cuvette ampule for use with automated chemical and microbiological analysis apparatuses. The nutrient containing ampule features an upper detachable stem and lower body portion which includes a pair of flat, uniformly spaced sides having the desired optical characteristics. One or more of the cuvette ampules is to be seated and maintained in a fixed position within a cartridge to facilitate insertion into analytical apparatuses. Breaking and removing the ampule stem provides an opening for receipt of the chemical or biological fluid to be evaluated. A compressible member covers each opening to seal the opened ampule and maintain the position of the ampule in the cartridge.

10 Claims, 6 Drawing Figures

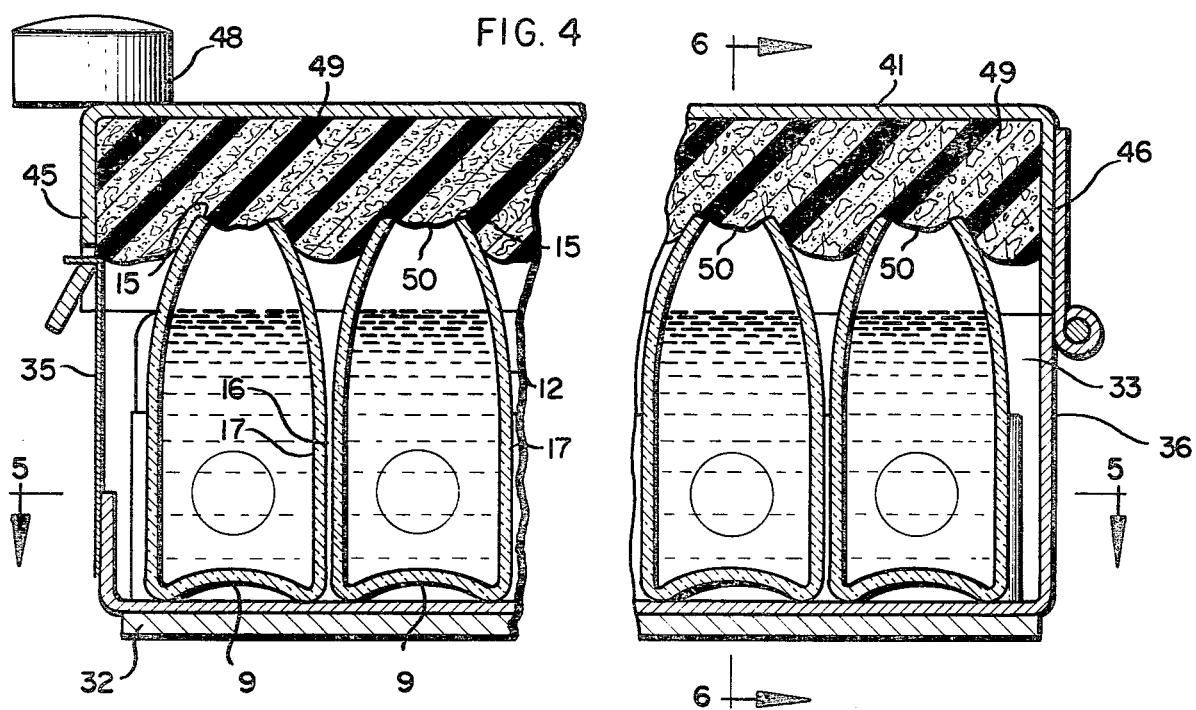
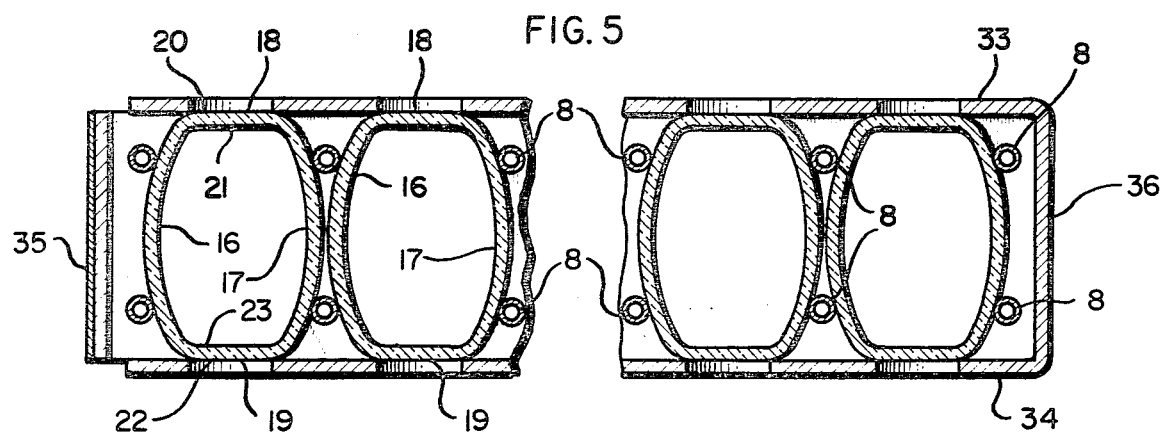
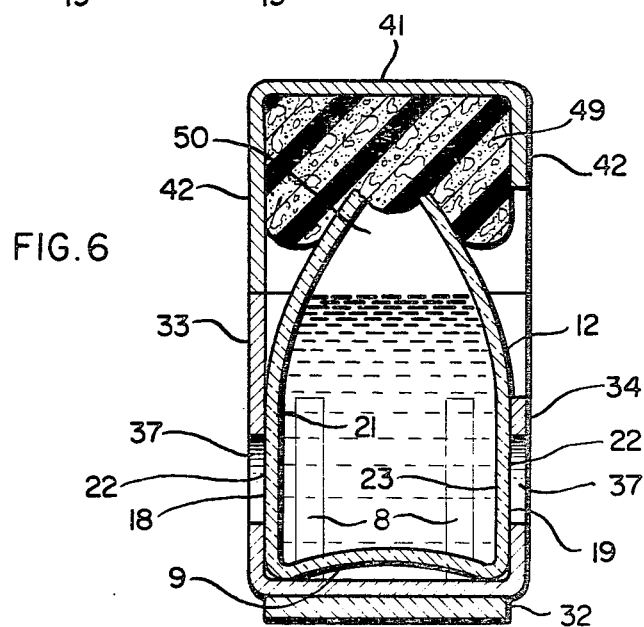

CUVETTE AMPULE FOR USE WITH AUTOMATIC ANALYZER APPARATUS

BACKGROUND OF THE INVENTION

The present invention relates generally to a new and improved disposable cuvette ampule for use with chemical and microbiological analysis apparatuses.

Biological fluid analyzers such as disclosed in U.S. Pat. Nos. Re. 28,800 and 3,718,439, are capable of performing antibiotic susceptibility testing, medical bacteriology procedures, clinical chemical analysis and other related procedures. When an evaluation is undertaken with this apparatus, a biological fluid to be evaluated, such as serum, plasma, urine or cerebrospinal fluid is inoculated into a prepared nutrient of reagent fluid and placed into a cuvette cartridge which is inserted into the analyzer apparatus. The bacterial growth rate for the fluid in the various cuvettes can then be monitored by means of a plurality of individual optical detector systems, each of which is in registration with its respective cuvette.

Electronic computation means such as computers and/or other computing devices well known in the art, are available to evaluate the output of the detection system and to make appropriate calculations, either through analog or digital means, to record and display the results in a meaningful and appropriate manner.

In certain uses, prior art cartridges employing a plurality of molded integral cuvettes are not desirable. Often, only a single cuvette is preferred to receive a specimen of biological fluid that is to be tested for bacterial content. Accordingly, it is unnecessary to employ a relatively expensive cartridge which utilizes a plurality of cuvettes.

Individual prior art containers for evaluating a biological fluid such as urine or the like are available; however, they suffer from a number of disadvantages including the fact that they are not particularly compatible with an automated analyzer apparatus of the type disclosed in U.S. Pat. No. 3,718,439.

One prior art system employs a device which includes a slide that is enclosed in an individual optically clear tube. The slide, which is impregnated with solid nutrients, is connected to and depends from a releasable top member that is screwed on to the tube. In operation, a biological fluid specimen to be evaluated is initially collected in a separate container. Next, the top member of the tube is unscrewed. Then the top member and the slide connected to it are withdrawn. The slide then is dipped in the container containing the specimen to be evaluated. Subsequently, the dipped slide is replaced in the tube and the top is screwed back to the tube. The tube is then visually reviewed and an evaluation is made as to the number of bacterial colonies growing on the nutrient. This particular prior art system is unsatisfactory for a quick, inexpensive determination of bacterial procedure. Initially, this particular procedure involves an excessive number of steps which is significant when one considers that the specimen evaluation procedures can vary among technicians who perform them. It is important to minimize any variations which may occur because of the proficiency of a technician conducting the multi-step evaluation.

While it is known to employ containers such as ampules to hold biological fluids, ampules presently available are not satisfactory because they do not have the desired structure which permits the ampule to be optically monitored for bacterial growth in an automater analyzer such as the one disclosed in U.S. Pat. No. 3,718,439.

What is desired is an individual, disposable cuvette which is adapted to be readily and easily placed in a cartridge, which in turn is adapted to be placed in an analyzer that monitors the contents of the ampule by means of an optical detection system. Moreover, it is desired that the individual cuvette be constructed as a unitary molded container having at least two uniformly spaced flat surfaces to produce a light path of uniform length to allow automated optical monitoring of any bacterial growth within the cuvette.

SUMMARY OF THE INVENTION

The invention disclosed and claimed herein serves to eliminate the problems associated with biological evaluation containers presently available. The present invention relates to a cuvette ampule which is adapted to receive a prepared nutrient reagent fluid. The ampule comprises a bottom or first portion and a neck extending upward from the first portion. A stem extends upward from the neck. Preferably, the lower portion of the stem is prescored so that the stem portion can be readily and easily disconnected from the remaining portion of the ampule to provide an opening in the ampule.

The bottom portion of the ampule of the present invention includes two molded substantially flat interior and exterior wall surfaces which provide the desired optical characteristics.

At the time the ampule is made, a measured amount of prepared nutrient is deposited in the bottom portion of the ampule. Subsequently, the stem portion of the ampule is drawn to close off the top and the ampule and contents are terminally batched sterilized. The closed, sterilized container is storage stable until opened for use.

In use, one or more cuvette ampules are placed in a cartridge. The cartridge of the present invention is partitioned to seat each ampule in a fixed position. The ampule is situated in the catridge so that the optical flat wall surfaces of the bottom portion of the ampule are aligned with the optical detection system when the ampule and cartridge are placed in the analyzer apparatus. The stem of the ampule is then snapped or broken off at the area of a prescored line located near the ampule neck. The nutrient, located in the bottom portion of the ampule is then seeded with a set volume of biological fluid to be evaluated. Subsequently, the cartridge top is closed so that it covers and seals the open top of each ampule seated in the cartridge. The cartridge is placed in the analyzer apparatus and the bacterial growth rate for the fluid in each ampule is monitored by means of an optical detector system which is in registration with each respective ampule.

The ampule and cartridge of the present invention permit the utilization of a relatively inexpensive, one-piece integral, disposable ampule. The ampule can be manufactured for use with standard filling equipment which fills the ampule with a predetermined amount of nutrient. Similarly, the ampule of the present invention can be of a size that will permit it to be utilized with conventional ampule sterilization equipment. Moreover, the ampule, upon receipt of the nutrient, can be sealed and stored until it is opened to receive the biological fluid to be evaluated.

BRIEF DESCRIPTION OF THE DRAWINGS

The invention together with its further objects and advantages thereof may be best understood by reference to the following descriptions taken in conjunction with the accompanying drawings, in which like reference numerals identify like elements in the several figures and in which:

FIG. 4 shows a partial sectional view of the ampules disposed in the cartridge taken along line 4—4 in FIG. 3;

FIG. 5 shows a partial sectional view of the ampules disposed within the cartridge taken along lines 5—5 in FIG. 4; and, FIG. 6 shows a partial end sectional view of an ampule disposed within the cartridge taken along line 6—6 in FIG. 4.

DETAILED DESCRIPTION

Figure 1:
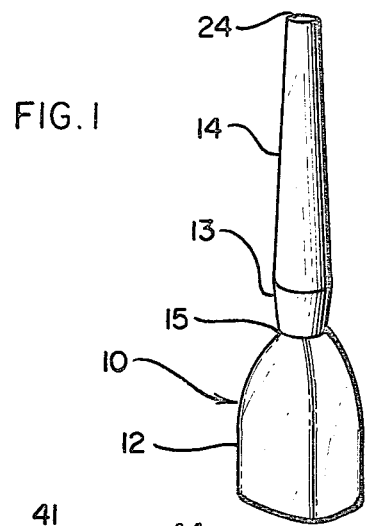
FIG. 1 shows a perspective view of the ampule of the present invention.

Referring to the drawings, cuvette ampule 10 is adapted to be seated and retained in cartridge 11. Ampule 10 preferably is made of glass or other suitable material which is capable of being molded, heat sterilized and sealed without additional material. It comprises a bottom or first portion 12, a neck section 13 located above the bottom portion, and a relatively long narrow tapered stem 14 which extends upwardly from the neck section. Preferably, the neck section is prescored at 15 so that when an appropriate force is applied to the stem, the stem will snap off and be removed from ampule 10 at the location of the prescored area 15.

The bottom portion of ampule 10, as seen more clearly in FIGS. 4–6, includes bottom wall 9, opposed side walls 16, 17, and opposed end walls 18 and 19. Sides 16 and 17 are arcuate shaped with the arcs projecting outwardly away from the center of the ampule. End wall 18 includes substantially flat faces 20, 21 while end wall 19 includes substantially flat faces 22, 23. The flat faces 20-23 on end walls 18 and 19 are molded so that they will be aligned with each other when ampule 10 is seated in cartridge 11. Further, the flat faces are each of a sufficient length to provide the desired optical characteristics when the ampule is monitored by an optical detector system which is in registration with ampule end walls 18 and 19. The use of flat walls gives the light a straight path. This is the most reproducible type of optical surface.

When ampule 10 is molded, ampule stem 14 initially is drawn to provide an opened tapered top 24. The small opening is left in the top of stem 14 so that a measured amount of nutrient can enter the ampule through the opening. The nutrient rests in bottom portion 12. Subsequently, the stem is drawn together at its tip to provide a closed, leak-free container which can then be sterilized and stored on the shelf until needed.

Ampule 10 is adapted to be seated in cartridge 11 which comprises ampule seating member 30 and hinged closure member 31. Cartridge closure member 30 includes a bottom wall 32 which is substantially longer than it is wide. A plurality of spaced and aligned pegs extend upwardly from the floor of bottom wall 32. Opposed, spaced side walls 33, 34 are connected to and extend upwardly from bottom wall 32, and first and second end walls 35, 36 are connected to the side walls.

Side walls 33 and 34 include a plurality of spaced apertures 37 which are aligned with each other. It will be observed from FIGS. 1, 5, and 6 that when an ampule 10 of the present invention is inserted in cartridge 11, the flat faces 20-23 of ampule ends 18, 19 are aligned with a pair of opposed apertures 37 so that the desired optical monitoring can be achieved.

Hinge 38 is joined to cartridge end 36 while a spring arm 39 and latch 40 extend upward from end 35.

Cartridge closure member 31 comprises a top wall 41. Wall 41, like bottom wall 32, has a length which is substantially longer than it is wide. Side wall 42, FIG. 6, and side wall sections 43, 44 extend downwardly from top wall 41. Walls 45, 46 are located at the respective ends of top closure member 31.

End wall 45 has an opening 47 which is adapted to receive latch 40. A knob or handle 48 is joined to top wall 41 and extends outwardly beyond closure end wall 45. End wall 46 is connected to end wall 36 by means of hinge 38 to provide a hinged connection between closure members 30, 31.

A compressible member 49 fashioned from a material such as foam is situated in the recess formed by the top, side and end walls of top cartridge closure member 31. The compressible member can be glued, friction fit or secured in place by any suitable means. The thickness of the compressible member, in an uncompressed state, is such that, when an ampule 10 with its stem removed is positioned in a closed cartridge 11, the foam will cover the opening 50 in the ampule and will be compressed sufficiently to provide a substantially leak-free seal between the ampule and foam member. It is also important that the compressible member be of sufficient substance so that when it is in a compressed state, it is capable of maintaining the alignment of the ampule during agitation. This compressible feature of the foam member 49 is seen more clearly in FIGS. 4 and 6 where the foam member covers the opening 50 which occurs when the stem is removed from ampule 10.

OPERATION

When it is desired to evaluate one or more specimens of biological fluid, the necessary number of ampules with the nutrients disposed within them are opened by snapping the stem 14 off the top of the ampule. The ampule is inserted in the bottom member 32 of cartridge II and is retained in position by means of pegs 8 which abut ampule side walls 16, 17.

Figure 2:
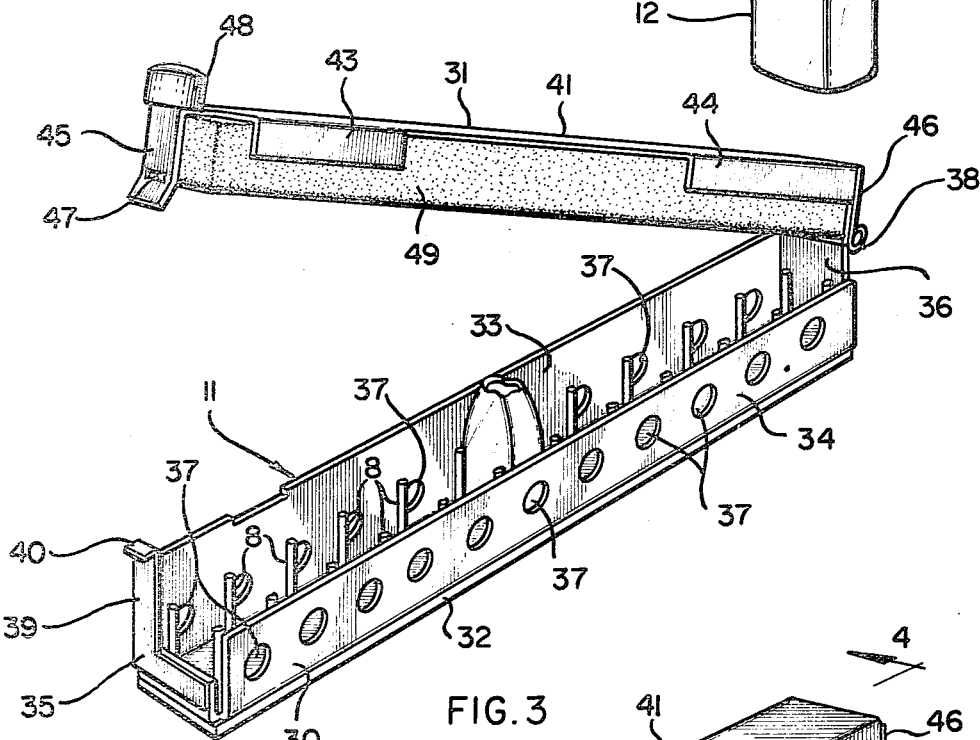
FIG. 2 shows a perspective view of an ampule of FIG. 1 with its stem portion removed and the ampule disposed within the cartridge of the present invention.
Figure 3:
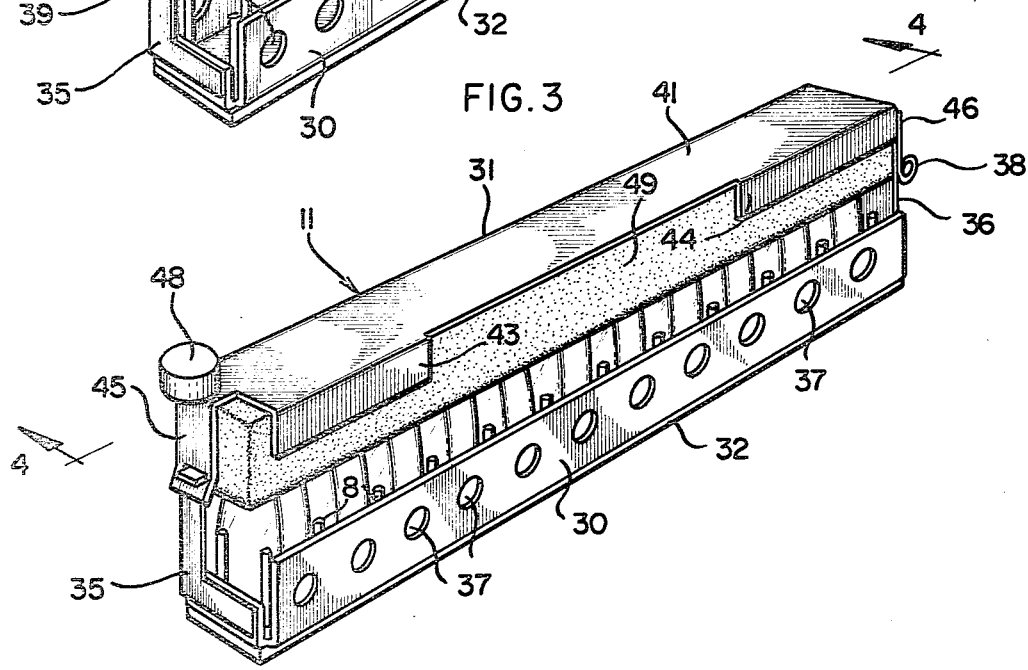
FIG. 3 shows a perspective view of the cartridge of FIG. 2 in a closed position with the cartridge top closed over a plurality of ampules disposed with the cartridge.

A measured volume of biological fluid then is deposited in ampule 10 through opening 50 and mixes with the nutrient. Top closure member 31 is pivoted downward and is closed and locked in position by pressing knob 48 downward until with latch 40 enters opening 47. The latch locks the top closure member 41 in position relative to bottom closure member 30 as seen clearly in FIGS. 1 and 2. Compressible member 49, which is in a compressed state when the cartridge is in a closed locked position, serves to seal ampule opening 50 to prevent any fluid from escaping from ampules 10 and any movement of the ampule.

Loaded cartridge II is inserted in the analyzer apparatus of the type disclosed in U.S. Pat. No. 3,718,439 and the desired evaluation is completed. Once the necessary measurements are made, the cartridge can be removed from the analyzer apparatus and the ampules 10 and compressible member 49 can be discarded.

While a particular cartridge has been illustrated in the drawings it is appreciated that variations can be made in it by one skilled in the art. For example, the apertures 37 could be removed and replaced by a slot which would extend along a substantial portion of the length of side walls 33, 34. Similarly, it is appreciated that the cartridge could be modified to conform to the particular cartridge receiving station in the analyzer apparatus. Moreover, the cartridge can be made of any suitable metal or plastic material.

The compressible member can be made of any suitable material such as polyolefin. Essentially, the foam serves as a fluid stopper and can be used with ampules having jagged edges and with ampules which, when seated in cartridge 11, vary in height. The foam member serves to seal the ampule and place pressure on it to hold it in position in the cartridge.

The foregoing detailed description has been given for clearness of understanding only, and no unnecessary limitations should be understood therefrom, as modifications will be obvious to those skilled in the art.

What is claimed is:

1. A sealed cuvette ampule for use with an optical scanning analyzer apparatus of biological fluids, said ampule comprising:
   (a) a bottom portion having a pair of spaced aligned substantially flat walls;
   (b) said flat walls comprising a material which permits the passage of light beams through said walls;
   (c) a neck section extending from the top of said bottom portion;
   (d) a removable stem connected to said neck section; and,
   (e) said ampule further including a nutrient enclosed within said ampule,
   whereby upon removal of said stem, an opening is provided in said ampule which permits the receipt of a biological fluid into said cuvette ampule to mix with said nutrient.

2. A cuvette ampule in accordance with claim 1 wherein said cuvette ampule bottom portion, neck and stem comprise a unitary integral one piece glass member.

3. A cuvette ampule in accordance with claim 2, wherein said stem is tapered.

4. A cuvette ampule in accordance with claim 1 and further including a cartridge to be inserted in biological fluid analysis apparatus, said cartridge comprising;
   (a) a cuvette ampule receiving bottom member and a top closure member to be positioned over said receiving member;
   (b) said bottom member including means for seating and positioning one or more of said cuvette ampules in said cartridge;
   (c) means for permitting the passage of light through said cartridge bottom member and said ampule flat walls;
   (d) said top cartridge member being to be closed upon said bottom cartridge member; and,
   (e) said top cartridge member including a compression and sealing means for maintaining one or more ampules in fixed position relative to each other in said cartridge and for sealing the opening in each of said ampules when said ampule stem is removed.

5. The cuvette ampule and cartridge of claim 4 wherein said bottom closure member seating and positioning means include a plurality of spaced pegs.

6. The cuvette ampule and cartridge of claim 4 wherein a plurality of ampule cuvettes are disposed within said cartridge.

7. The cuvette ampule and cartridge of claim 4 wherein said cartridge top closure member is pivotally connected to said cartridge cuvette ampule receiving bottom member.

8. The cuvette cartridge of claim 4 wherein said cartridge is substantially longer than it is wide.

9. The cuvette cartridge of claim 4 wherein at least one ampule is disposed within said cartridge having a stem removed and said cartridge top member is closed over said cartridge bottom member with said compression and sealing means being disposed over said stemless ampule to maintain said ampule in a fixed position in said cartridge and said stemless cuvette ampule is sealed at its opening by said cartridge sealing means to provide a substantially leak-free ampule.

10. The cuvette ampule and cartridge of claim 9 wherein said cartridge sealing and compression means includes a compressible cell foam material disposed within said cartridge top member.

* * * * *